(12) United States Patent
Zhou et al.

(10) Patent No.: US 10,906,933 B2
(45) Date of Patent: Feb. 2, 2021

(54) COUPLED PEPTIDE CHAIN FOR DISSOLVING POORLY SOLUBLE POLYPEPTIDES AND APPLICATION THEREOF FOR SEPARATION AND PURIFICATION IN LIQUID CHROMATOGRAPHY

(71) Applicant: Spec-Chem Industry Inc., Jiangsu (CN)

(72) Inventors: Bin Zhou, Jiangsu (CN); Jiansheng Zha, Jiangsu (CN); Wu Kang, Jiangsu (CN); Jinrong Xu, Jiangsu (CN); Yi Pan, Jiangsu (CN)

(73) Assignee: SPEC-CHEM INDUSTRY INC., Jiangsu (CN)

( * ) Notice: Subject to any disclaimer, the term of this patent is extended or adjusted under 35 U.S.C. 154(b) by 32 days.

(21) Appl. No.: 15/739,544

(22) PCT Filed: Feb. 3, 2016

(86) PCT No.: PCT/CN2016/073393
§ 371 (c)(1),
(2) Date: Dec. 22, 2017

(87) PCT Pub. No.: WO2017/020568
PCT Pub. Date: Feb. 9, 2017

(65) Prior Publication Data
US 2018/0186830 A1    Jul. 5, 2018

(30) Foreign Application Priority Data

Jul. 31, 2015  (CN) .......................... 2015 1 0466145

(51) Int. Cl.
| | |
|---|---|
| C07K 1/16 | (2006.01) |
| C07K 2/00 | (2006.01) |
| C07K 7/08 | (2006.01) |
| C07K 7/06 | (2006.01) |
| C07K 1/107 | (2006.01) |
| B01J 20/292 | (2006.01) |
| C07K 17/06 | (2006.01) |
| G01N 30/88 | (2006.01) |
| G01N 30/34 | (2006.01) |
| C07C 63/06 | (2006.01) |
| G01N 33/68 | (2006.01) |
| G01N 30/02 | (2006.01) |

(52) U.S. Cl.
CPC .............. *C07K 1/16* (2013.01); *B01J 20/292* (2013.01); *C07K 1/107* (2013.01); *C07K 2/00* (2013.01); *C07K 7/06* (2013.01); *C07K 7/08* (2013.01); *C07K 17/06* (2013.01); *B01J 2219/00916* (2013.01); *C07C 63/06* (2013.01); *C07K 2319/00* (2013.01); *G01N 30/34* (2013.01); *G01N 33/6803* (2013.01); *G01N 2030/027* (2013.01); *G01N 2030/8831* (2013.01)

(58) Field of Classification Search
None
See application file for complete search history.

(56) References Cited

FOREIGN PATENT DOCUMENTS

| | | |
|---|---|---|
| CN | 1098416 | 2/1995 |
| CN | 105001307 | 10/2015 |

OTHER PUBLICATIONS

X Li, et al.; Resins With Hydroxyl Groups Used in Solid-Phase Organic Synthesis; Ion Exchange and Adsorption; Oct. 28, 2002; p. 472; lines 13-20; vol. 18, No. 5 (with partial English translation).
Written Opinion and International Search Report for International patent application No. PCT/CN2016/073393 dated May 5, 2016; 11 pages.

*Primary Examiner* — Thomas S Heard
(74) *Attorney, Agent, or Firm* — Rankin, Hill & Clark LLP

(57) ABSTRACT

The invention discloses a coupled peptide chain for dissolving poorly soluble polypeptides and an application thereof for separation and purification in liquid chromatography, belonging to the field of biochemistry. A special linker arm is used to link a hydrophilic polypeptide chain with a poorly soluble polypeptide chain to solve the problem that the poorly soluble polypeptide chains cannot be operated in the liquid chromatography, and optimize the combination of hydrophilic amino acids, and then the poorly soluble polypeptide chain and hydrophilic polypeptide chain are broken by hydrolyzing an ester bond, so that the target peptide chain is directly precipitated, the method has the characteristics of simplicity and high efficiency, and the poorly soluble polypeptide product obtained by the method fully meets the standards required by customers.

8 Claims, 2 Drawing Sheets
Specification includes a Sequence Listing.

COUPLED PEPTIDE CHAIN FOR DISSOLVING POORLY SOLUBLE POLYPEPTIDES AND APPLICATION THEREOF FOR SEPARATION AND PURIFICATION IN LIQUID CHROMATOGRAPHY

TECHNICAL FIELD

The present invention relates to the fields of bioengineering and polypeptide production, and more particularly to a coupled peptide chain for dissolving poorly soluble polypeptides and an application thereof for separation and purification in liquid chromatography.

BACKGROUND ART

Solubility is a relatively important issue encountered during studying proteins and polypeptides, and each amino acid has its own inherent chemical properties. For embodiment, leucine, isoleucine and valine are hydrophobic while lysine, histidine and arginine are hydrophilic. Poorly soluble polypeptides are mainly caused by poorly soluble amino acids contained therein, and in general, poorly soluble amino acids accounting for more than 75% of the amino acids of polypeptides renders the polypeptides poorly soluble.

In terms of polypeptide production and preparation, poor solubility has long been a big problem in polypeptide separation and purification steps. The main purification means for polypeptides is reversed-phase high performance liquid chromatography, which has the characteristics of good separation effect, high resolution and high recovery rate. In reversed-phase high performance liquid chromatography, polypeptides need to be completely dissolved in a solvent when the polypeptides are subjected to separation and purification, and the most suitable conventional solvents are $H_2O$ and ACN, so that an effective separation and purification can be performed by reversed-phase high performance liquid chromatography; however, poorly soluble polypeptides bring great trouble to the majority of researchers in the operation.

In the existing method for solving the problem of the purification of the poorly soluble polypeptides, a good organic solvent (for embodiment, DMSO and DMF) can only be selected to dissolve the polypeptides and then separation and purification by reverse-phase high performance liquid chromatography are conducted. However, DMF or DMSO improves dissolution by destroying the secondary structure of polypeptides, resulting in a greatly reduced separation effect of the high performance liquid chromatography, and has a limited dissolving ability for poorly soluble peptide chains.

SUMMARY OF THE INVENTION

Objectives of the present invention: an objective of the present invention is to provide a coupled peptide chain for dissolving poorly soluble polypeptides; and a further objective of the present invention is to provide an application of the coupled peptide chain in dissolving poorly soluble polypeptides.

Technical solution: in order to achieve the above-mentioned objectives, a coupled peptide chain for dissolving poorly soluble polypeptides of the present invention is as shown in formula (I):

$$\text{X-Ph-Y}—(B)_n \quad (I),$$

wherein Ph represents a phenyl ring substituted at 1 and 4 positions;

X represents a hydroxy group or a C1-C4 monohydroxy alkyl group;

Y represents a carbonyl group or a C2-C4 carbonylalkyl group formed after the dehydration and condensation reaction with $(B)_n$;

$(B)_n$ represents a hydrophilic polypeptide chain formed by the condensation of n identical or different hydrophilic amino acids, and n is 1.2 to 2 times the number of amino acids of the poorly soluble polypeptide.

In particular, X of formula (I) is any one of a linear or branched —$CH_2OH$, —$CH_2CH_2OH$, —$CH_2CH_2CH_2OH$ or —$CH_2CH_2CH_2CH_2OH$; and Y is any one of a linear or branched —$CH_2CO$—, —$CH_2CH_2CO$— or —$CH_2CH_2CH_2CO$—.

X-Ph-Y is originally derived from a phenyl ring substituted with monohydroxyalkyl and monocarboxyalkyl respectively at 1 and 4 positions. The —OH of the carboxyl group and the amino group of $(B)_n$ are dehydrated and condensed to form a peptide chain, and thus the Y of general formula (I) is any one of a linear or branched —$CH_2CO$—, —$CH_2CH_2CO$— or —$CH_2CH_2CH_2CO$—.

In the coupled peptide chain of the present invention, X-Ph-Y is a "linker arm" for coupling the hydrophilic polypeptide chain with the poorly soluble polypeptide chain, and this "linker arm" is from any one of 4-hydroxybenzoic acid, p-hydroxymethylbenzoic acid, 4-(2-hydroxyethyl)benzoic acid, 4-(3-hydroxypropyl)benzoic acid, 4-(4-hydroxybutyl)benzoic acid, p-hydroxyphenylacetic acid, 4-(hydroxymethyl)phenylacetic acid, p-hydroxyphenylpropionic acid, 3-[4-(hydroxymethyl)phenyl]propionic acid, 4-(4-hydroxyphenyl)butyric acid, 2-(4-hydroxyphenyl)propionic acid, 3-(4-hydroxyphenyl)butyric acid, 2-[(4-hydroxyphenyl)methyl]aminobutanoic acid and 4-(1-hydroxyethyl)-benzoic acid, and is linked to the N-terminal of the hydrophilic polypeptide chain after a dehydration condensation reaction.

In addition, in the coupled peptide chain of the present invention, hydrophilic amino acids include, but are not limited to, any one of arginine, lysine, asparagine, aspartic acid, glutamine, glutamic acid, histidine and proline, and these amino acids are shown in Table 1 below and have a very small hydrophobic parameter. The poorly soluble polypeptide chain can be understood as a polypeptide chain containing poorly soluble amino acids and having a low or poor solubility in liquid chromatography. The poorly soluble amino acids include any one of alanine, methionine, cysteine, phenylalanine, leucine, valine and isoleucine, and these amino acids are shown in Table 2 and have a large hydrophobic parameter contain, and polypeptide chains containing these amino acids generally have a very low solubility.

TABLE 1

List of hydrophilic amino acids

| Name of amino acids | Abbreviation | Code | Hydrophobic parameter |
|---|---|---|---|
| Arginine | Arg | R | −4.5 |
| Lysine | Lys | K | −3.9 |
| Asparagine | Asn | N | −3.5 |
| Aspartic acid | Asp | D | −3.5 |
| Glutamine | Gln | Q | −3.5 |
| Glutamic acid | Glu | E | −3.5 |
| Histidine | His | H | −3.2 |
| Proline | Pro | P | −1.6 |

TABLE 2

List of poorly soluble amino acids

| Name of amino acids | Abbreviation | Code | Hydrophobic parameter |
|---|---|---|---|
| Alanine | Ala | A | 1.8 |
| Methionine | Met | M | 1.9 |
| Cysteine | Cys | C | 2.5 |
| Phenylalanine | Phe | F | 2.8 |
| Leucine | Leu | L | 3.8 |
| Valine | Val | V | 4.2 |
| Isoleucine | Ile | I | 4.5 |

The above-mentioned poorly soluble polypeptide chain is generally the target product in the synthesis of peptide chains, and the hydrophilic polypeptide chain and the linker arm may be optimized in connection with production practice. As a further optimization of the present invention, the X-Ph-Y is from any one of 4-hydroxybenzoic acid, p-hydroxymethylbenzoic acid, 4-(2-hydroxyethyl)benzoic acid, p-hydroxyphenylacetic acid and 4-(hydroxymethyl)phenylacetic acid, and is linked to the N-terminal of the hydrophilic polypeptide chain after a dehydration condensation reaction. The hydrophilic amino acid in the hydrophilic polypeptide chain is preferably glutamic acid or aspartic acid. When the total number of glutamic acid and/or aspartic acid accounts for 30% to 80% of the total number of hydrophilic amino acids, the best effect is achieved by using X-Ph-Y— $(B)_n$ in separation and purification by liquid chromatography, and finally hydrolyzing an ester bond.

The steps for separation and purification by using the above-mentioned coupled peptide chain in the present invention are as follows:

(1) firstly synthesizing a hydrophilic polypeptide chain by a solid-phase synthesis method, then synthesizing a linker arm and an poorly soluble polypeptide chain, and after treatment, obtaining a crude product of poorly soluble polypeptide chain-linker arm-hydrophilic polypeptide chain;

(2) dissolving the above product with water/acetonitrile, and loading same for separation and purification by high performance liquid chromatography, and vacuum freeze drying the same to obtain a pure product; and (3) subjecting the above pure product with ester bond hydrolysis by using an LiOH saturated solution, after reacting at room temperature for 3 hours, precipitating the target polypeptide chain, and filtrating and drying the same to obtain the finished product.

Since the hydrophilicity of X-Ph-Y—$(B)_n$ is strong, and peptide chains are mostly acidic, the dissolution effect thereof in LiOH is very outstanding. Moreover, high contents of glutamic acid and aspartic acid in the hydrophilic polypeptide chain facilitate the dissolution of the hydrophilic polypeptide chain in an alkaline solution, and improve the precipitation effect of the target polypeptide chain.

Some common abbreviations and the meanings thereof in the present invention are as follows:
HMBA 4-hydroxymethylbenzoic acid, a linker arm;
DIC N,N'-diisopropylcarbodiimide, a condensation agent;
DMAP 4-dimethylaminopyridine, as a supernucleophilic catalyst, for increasing the linking efficiency of hydroxyl and carboxyl groups;
HOBT 1-hydroxybenzotriazole, used for preventing racemization and reducing side effects;
DMF dimethylformamide, a reaction solvent;
TFA trifluoroacetic acid, used for lysing polypeptides and resins;
TIS triisopropylsilane, for better removal of amino acid protecting groups;
EDT ethanedithiol, for better removal of amino acid protecting groups;
ACN acetonitrile, for increasing the solubility of polypeptides in an aqueous solution;
Fmoc N-fluorenylmethoxycarbonyl, a protecting group for a functional group;
Pbf [(2,3-dihydro-2,2,4,6,7-pentamethylbenzofuran-5-yl) sulfonyl, a protecting group for α-amino group;
Boc t-butyloxycarboryl, a protecting group for α-amino group;
Trt triphenylmethyl, a protecting group for α-amino group;
Otbu tert-butyl ester, a protecting group for α-amino group.

Beneficial effects: the present invention provides a solution for linking a hydrophilic polypeptide chain with a poorly soluble polypeptide chain by a special linker arm, thereby solving the problem that the poorly soluble polypeptide chains cannot be operated in the liquid chromatography. The coupled peptide chain of the present invention can be synthesized by a solid-phase synthesis method in both production and experiments, and also can be used as a tailor-made product that offers service for the production of target peptide chains. In particular, in the present invention, aiming at the characteristic of liquid chromatographic separation and purification environment, the combination of hydrophilic amino acids is optimized, and finally the poorly soluble polypeptide chain and hydrophilic polypeptide chain are broken by hydrolyzing an ester bond, so that the target peptide chain is directly precipitated, the method has the characteristics of simplicity and high efficiency, and the poorly soluble polypeptide product obtained by the method fully meets the standards required by customers.

DETAILED DESCRIPTION OF EMBODIMENTS

The present invention is further described below in conjunction with particular embodiments.

Embodiment 1

Figure 1:
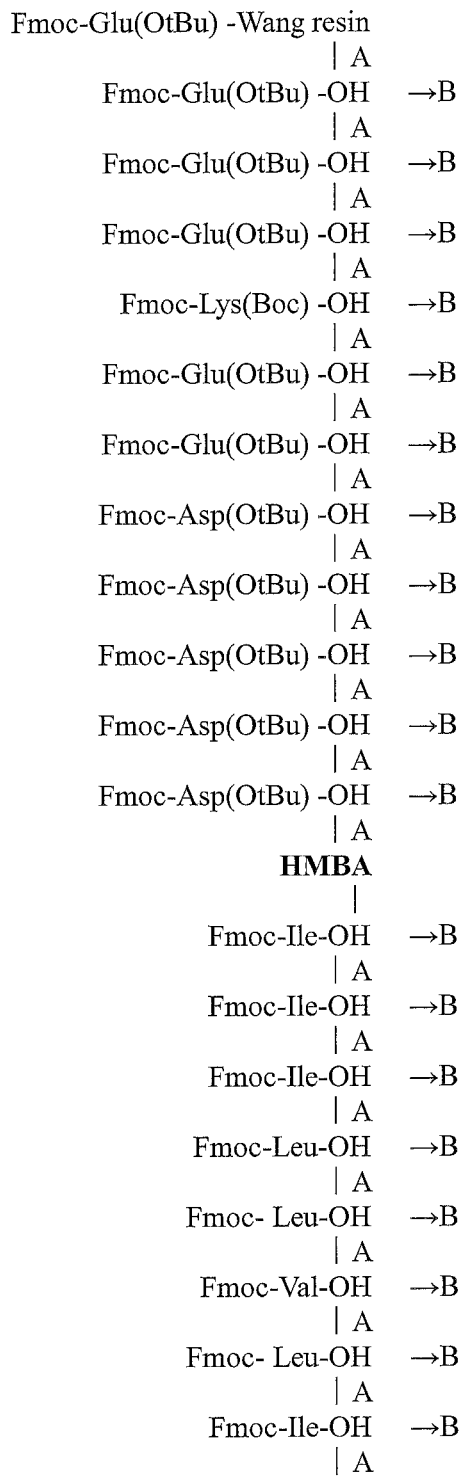
FIG. 1 is a schematic flow diagram of the polypeptide synthesis steps of embodiment 1 of the present invention.

This embodiment is directed to separation and purification of a poorly soluble polypeptide ILVLLIII (SEQ ID NO: 1), 4-hydroxymethylbenzoic acid was selected as a linker arm, and a hydrophilic polypeptide chain DDDDDEEKEEEE (SEQ ID NO: 2) was linked via the linker arm. D represents aspartic acid, having a hydrophobic parameter of −3.5, protecting the functional group with OtBu; E represents glutamic acid, with a hydrophobic parameter of −3.5, protecting the functional group with OtBu; K represents lysine, having a hydrophobic parameter of −3.9, protecting the functional group with Boc; and all of these amino acids were subjected to solid-phase synthesis by protecting α-amino group with Fmoc. As shown in FIG. 1, the specific synthesis steps are as follows:

1 g Fmoc-Glu(OtBu)-Wang resin was weighed, and [Operation A] was performed, i.e.: piperidine:DMF=1:4 (volume ratio) were added to remove the Fmoc protecting group at the N-terminal, the temperature was controlled at 30° C., the reaction was performed for 20 minutes, after the reaction, the resin was washed for three times with DMF/methanol respectively, a ninhydrin detection reagent was used for detection, and a color of blue indicated that the reaction was complete.

Then [Operation B] was performed, i.e.: DIC and HOBT which were two times the moles of the initial resin, and amino acids having protecting groups in an amount of two times of the initial resin were added for reacting for 1 hour, the temperature was controlled at 30° C., after the reaction was finished, the resin was washed for three times with DMF, and color detection by ninhydrin showing colorless indicated that the reaction was complete.

Subsequently, [Operation A] and [Operation B] were alternately performed, except that the hydrophilic amino acids added in [Operation B] were changed as the proceeding of the synthesis order. Glutamic acid, aspartic acid and lysine with protecting groups are respectively Fmoc-Glu(OtBu)-OH, Fmoc-Asp(OtBu)-OH and Fmoc-Lys(Boc)-OH. The reaction was thus performed until the linking of HMBA was complete, and color detection by a ninhydrin solution showing colorless indicated that the reaction was complete. A hydrophilic coupled peptide chain of X-Ph-Y—$(B)_n$ was obtained from the above reaction.

Based on the peptide chain obtained above, [Operation B] was directly performed, and was alternated with [Operation A] in the subsequent steps until Wang resin-poorly soluble polypeptide chain-linker arm-hydrophilic polypeptide chain was obtained.

Then the resin was lysed with 10 ml TFA:TIS:EDT=95%: 3%: 2% for 2 hours, and the protecting groups were removed from the coupled peptide chain. Then the resin was filtered to leave the mother liquor, and 100 ml diethyl ether was added thereto to precipitate polypeptide. A crude polypeptide was obtained after centrifuging at 3000 rpm for 2 minutes and precipitating, and after repeated washing and centrifugation, and then drying in a vacuum drier, a crude product of poorly soluble polypeptide chain-linker arm-hydrophilic polypeptide chain was obtained.

The above crude product was dissolved in a mixed liquid of water and acetonitrile, and loaded for separation and purification by high performance liquid chromatography, and after separation and purification by a gradient elution chromatographic system with $H_2O/0.1$ TFA % as the aqueous phase and ACN/0.1% TFA as the organic phase, target peaks were collected. The purity of the collected target peaks was detected by analytical high performance liquid chromatography. Qualified samples were concentrated by using a rotary evaporator and placed in a freezer to be pre-frozen into solids. Finally, the solids were placed into a vacuum freeze drier for lyophilization to obtain a pure product of ILVLLIII (SEQ ID NO: 1)-HMBA-DDDDDEEKEEEE (SEQ ID NO: 2).

The above pure product was subjected with ester bond hydrolysis by using an LiOH saturated solution, after reacting at room temperature for 3 hours, the target polypeptide chain ILVLLIII (SEQ ID NO: 1) was precipitated, while the added sequence HMBA-DDDDDEEKEEEE (SEQ ID NO: 2) was dissolved in the LiOH solution due to a strong hydrophilicity and the whole acidic peptide chains, and then the precipitated target polypeptide was filtrated and lyophilized to obtain the finished product.

In the above reactions, Fmoc amino acids were purchased from GL Biochem Co., Ltd., with the production batch number of GLS141015-4071, DIC Hobt DMAP was purchased from Suzhou Highfine Co., Ltd., HMBA was purchased from GL Biochem Ltd., TFA, TIS, EDT, ethyl ether, piperidine and DMF were all purchased from Nanjing Wanqing Co., Ltd.

Embodiment 2

Figure 2:
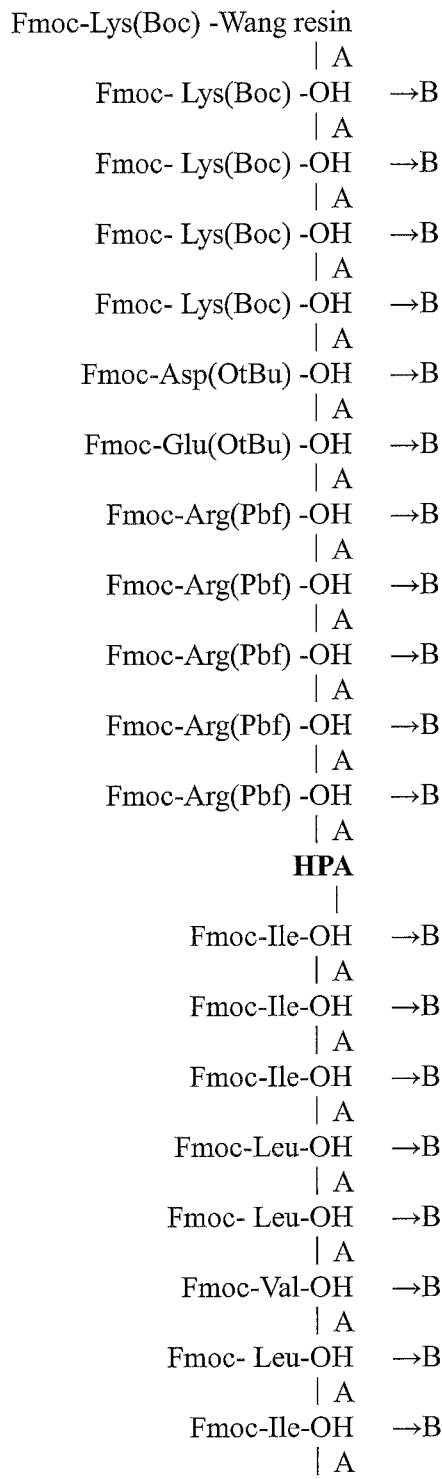
FIG. 2 is a schematic flow diagram of the polypeptide synthesis steps of embodiment 2 of the present invention.

The present embodiment is directed to separation and purification of a poorly soluble polypeptide ILVLLIII (SEQ ID NO: 1), 4-(2-hydroxyethyl)benzoicacid (HPA) was selected as a linker arm, and a hydrophilic polypeptide chain RRRRREDKKKKK (SEQ ID NO: 3) was linked via the linker arm. D represents aspartic acid, having a hydrophobic parameter of −3.5, protecting the functional group with OtBu; E represents glutamic acid, having a hydrophobic parameter of −3.5, protecting the functional group with OtBu; K represents lysine, having a hydrophobic parameter of −3.9, protecting the functional group with Boc; R represents arginine, having a hydrophobic parameter of −4.5, protecting the functional group with Pbf; and all of these amino acids were subjected to solid-phase synthesis by protecting α-amino group with Fmoc. As shown in FIG. 2, the specific synthesis steps are as follows:

1 g Fmoc-Lys(boc)-Wang resin was weighed, and [Operation A] was performed, i.e.: piperidine:DMF=1:4 (volume ratio) were added to remove the Fmoc protecting group at the N-terminal, the temperature was controlled at 30° C., the reaction was performed for 20 minutes, after the reaction, the resin was washed for three times with DMF/methanol respectively, a ninhydrin detection reagent was used for detection, and a color of blue indicated that the reaction was complete.

Then [Operation B] was performed, i.e.: DIC and HOBT which were two times the moles of the initial resin, and amino acids having protecting groups in an amount of two times of the initial resin were added for reacting for 1 hour, the temperature was controlled at 30° C., after the reaction was finished, the resin was washed for three times with DMF, and color detection by ninhydrin showing colorless indicated that the reaction was complete.

Subsequently, [Operation A] and [Operation B] were alternately performed, except that the hydrophilic amino acids added in [Operation B] were changed as the proceeding of the synthesis order. Lysine, aspartic acid, glutamic acid and arginine with protecting groups are respectively Fmoc-Lys(Boc)-OH, Fmoc-Asp(OtBu)-OH, Fmoc-Glu(OtBu)-OH and Fmoc-Arg(Pbf)-OH. The reaction was thus performed until the linking of HPA was complete, and color detection by a ninhydrin solution showing colorless indicated that the reaction was complete. A hydrophilic coupled peptide chain of X-Ph-Y—$(B)_n$ was obtained from the above reaction.

Based on the peptide chain obtained above, [Operation B] was directly performed, and was alternated with [Operation A] in the subsequent steps until Wang resin-poorly soluble polypeptide chain-linker arm-hydrophilic polypeptide chain was obtained.

Then the resin was lysed with 10 ml TFA:TIS:EDT=95%: 3%: 2% for 2 hours, and the protecting groups were removed from the coupled peptide chain. Then the resin was filtered to leave the mother liquor, and 100 ml diethyl ether was added thereto to precipitate polypeptide. A crude polypeptide was obtained after centrifuging at 3000 rpm for 2 minutes and precipitating, and after repeated washing and centrifugation, and then drying in a vacuum drier, a crude product of poorly soluble polypeptide chain-linker arm-hydrophilic polypeptide chain was obtained.

The above crude product was dissolved in a mixed liquid of water and acetonitrile, and loaded for separation and purification by high performance liquid chromatography, and after separation and purification by a gradient elution chromatographic system with $H_2O$/0.1 TFA % as the aqueous phase and ACN/0.1% TFA as the organic phase, target peaks were collected. The purity of the collected target peaks was detected by analytical high performance liquid chromatography. Qualified samples were concentrated by using a rotary evaporator and placed in a freezer to be pre-frozen into solids. Finally, the solids were placed into a vacuum freeze drier for lyophilization to obtain a pure product of ILVLLIII (SEQ ID NO: 1)-HPA-RRRRREDKKKKK (SEQ ID NO: 3).

The above pure product was subjected with ester bond hydrolysis by using an LiOH saturated solution, after reacting at room temperature for 3 hours, the target polypeptide chain ILVLLIII (SEQ ID NO: 1) was precipitated, while the added sequence HPA-RRRRREDKKKKK (SEQ ID NO: 3) was dissolved in the LiOH solution due to a strong hydrophilicity and the whole acidic peptide chains, and then the precipitated target polypeptide was filtrated and lyophilized to obtain the finished product.

Test Embodiment

This test evaluated the dissolving capacity of each group of peptide chain at 2 mg/mL in a DMF solution, a DMSO solution, an ACN:$H_2O$ (1:3) solution in HPLC, and an LiOH saturated solution, respectively. The poorly soluble polypeptide chain-linker arm-hydrophilic polypeptide chain in embodiments 1 and 2 were taken as Groups 1 and 2, respectively, and a separate poorly soluble polypeptide chain ILVLLIII (SEQ ID NO: 1) was taken as a control group, as shown in Table 3:

TABLE 3

Dissolving capacity evaluation after the treatment of the poorly soluble polypeptide chain

| Group | Peptide chain | DMF | DMSO | ACN:$H_2O$ (1:3) | LiOH saturated solution |
|---|---|---|---|---|---|
| 1 | ILVLLIII (SEQ ID NO: 1)-HMBA-DDDDDEEKEEEE (SEQ ID NO: 2) | completely dissolved, no solid precipitating | completely dissolved, no solid precipitating | completely dissolved, no solid precipitating | completely dissolved, no solid precipitating |
| 2 | ILVLLIII (SEQ ID NO: 1)-HPA-RRRRREDKKKKK (SEQ ID NO: 3) | partially dissolved, solids precipitating | partially dissolved, solids precipitating | completely dissolved, no solid precipitating | partially dissolved, solids precipitating |
| 3 | ILVLLIII (SEQ ID NO: 1) | very cloudy, solids precipitating | very cloudy, solids precipitating | very cloudy, solids precipitating | very cloudy, solids' precipitating |

The target peptide chain sequence was: ILVLLIII (SEQ ID NO: 1), which was very cloudy with solids precipitating after dissolving in DMF, DMSO and common HPLC purification condition of ACN: $H_2O$=1: 3. ILVLLIII (SEQ ID NO: 1) 4-HMBA-DDDDDEEKEEEE (SEQ ID NO: 2) was clear with no solids precipitating after dissolving in DMF, DMSO and common HPLC purification condition of ACN: $H_2O$ (1: 3). However, ILVLLIII (SEQ ID NO: 1)-HPA-RRRRREDKKKKK (SEQ ID NO: 3) was completely dissolved in ACN:$H_2O$ (1:3), but solids still precipitated in DMF and DMSO.

For the dissolution of the first group and second group of peptide chains in the LiOH saturated solution, it was best to require complete dissolving when adding, and then after waiting for 3 hours of reaction, the polypeptide chain hydrolysis was hydrolyzed to precipitate solids. Furthermore, the dissolution effect of the second group was obviously not better than that of the first group, which resulted in decreased product yield. It can be seen that the amino acid structure of the first group of hydrophilic polypeptide chain was more beneficial for the final precipitation of the poorly soluble polypeptide chain.

The above are merely preferred embodiments of the present invention, and it should be pointed out that for a person skilled in the art, some improvements and modifications can also be made under the premise of not departing from the principle of the present invention, and these improvements and modifications should also be considered to be within the protection scope of the present invention.

The invention claimed is:

1. A coupled peptide chain for dissolving poorly soluble polypeptides, wherein the peptide chain is as shown in formula (I):

$$X\text{-Ph-Y}\text{—}(B)_n \qquad (I),$$

wherein Ph represents a phenyl ring substituted at 1 and 4 positions;

X represents a hydroxy group or a C1, C3 or C4 monohydroxy alkyl group;

Y represents a carbonyl group or a C2-C4 carbonylalkyl group formed after the dehydration and condensation reaction with $(B)_n$;

$(B)_n$ represents a hydrophilic polypeptide chain formed by the condensation of n identical or different hydrophilic amino acids, and n is 1.2 to 2 times the number of amino acids of the poorly soluble polypeptide, wherein the hydrophilic amino acid is any one selected from a group consisting of arginine, lysine, asparagine, aspartic acid, glutamine, glutamic acid, histidine and proline, wherein the total number of glutamic acid or aspartic acid accounts for 30% to 80% of the total number of hydrophilic amino acids, and wherein the hydrophilic polypeptide chain includes DDDDDEEKEEEE (SEQ ID NO: 2).

2. A coupled peptide chain for dissolving poorly soluble polypeptides according to claim 1, wherein X is any one selected from a group consisting of a linear or branched —CH$_2$OH, —CH$_2$CH$_2$OH and —CH$_2$CH$_2$CH$_2$OH; and Y is any one selected from a group consisting of a linear or branched —CH$_2$CO—, —CH$_2$CH$_2$CO— and —CH$_2$CH$_2$CH$_2$CO—.

3. A coupled peptide chain for dissolving poorly soluble polypeptides according to claim 2, wherein the X-Ph-Y is any one selected from a group consisting of 4-hydroxybenzoic acid, p-hydroxymethylbenzoic acid, 4-(3-hydroxypropyl)benzoic acid, 4-(4-hydroxybutyl)benzoic acid, p-hydroxyphenylacetic acid, 4-(hydroxymethyl)phenylacetic acid, p-hydroxyphenylpropionic acid, 3-[4-(hydroxymethyl)phenyl]propionic acid, 4-(4-hydroxyphenyl)butyric acid, 2-(4-hydroxyphenyl)propionic acid, 3-(4-hydroxyphenyl)butyric acid, and 2-[(4-hydroxyphenyl)methyl]aminobutanoic acid.

4. A method for using the coupled peptide chain according to claim 1, comprising performing liquid chromatographic separation and purification of the poorly soluble polypeptide coupled with the peptide chain.

5. A coupled peptide chain for dissolving poorly soluble polypeptides according to claim 1, wherein the hydrophilic polypeptide chain is DDDDDEEKEEEE (SEQ ID NO: 2).

6. A coupled peptide chain for dissolving poorly soluble polypeptides, wherein the peptide chain is as shown in formula (I):

$$X\text{-Ph-Y}\text{—}(B)_n \qquad (I),$$

wherein Ph represents a phenyl ring substituted at 1 and 4 positions;

X is —CH$_2$CH$_2$OH;

Y is any one selected from a group consisting of a linear or branched —CH$_2$CO—, —CH$_2$CH$_2$CO— and —CH$_2$CH$_2$CH$_2$CO—; and (B)$_n$ represents a hydrophilic polypeptide chain formed by the condensation of n identical or different hydrophilic amino acids, and n is 1.2 to 2 times the number of amino acids of the poorly soluble polypeptide, wherein the hydrophilic amino acid is any one selected from a group consisting of arginine, lysine, asparagine, aspartic acid, glutamine, glutamic acid, histidine and proline, and wherein the hydrophilic polypeptide chain includes RRRRREDKKKKK (SEQ ID NO: 3).

7. A coupled peptide chain for dissolving poorly soluble polypeptides according to claim 6, wherein the X-Ph-Y is one selected from a group consisting of 4-(2-hydroxyethyl) benzoic acid and 4-(1-hydroxyethyl)-benzoic acid.

8. A coupled peptide chain for dissolving poorly soluble polypeptides according to claim 6, wherein the hydrophilic polypeptide chain is RRRRREDKKKKK (SEQ ID NO: 3).

* * * * *

SEQUENCE LISTING

<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: Poorly soluble polypeptide

<400> SEQUENCE: 1

Ile Leu Val Leu Leu Ile Ile Ile
1               5

<210> SEQ ID NO 2
<211> LENGTH: 12
<212> TYPE: PRT
<213> ORGANISM: Artificial Sequence
<220> FEATURE:
<223> OTHER INFORMATION: hydrophilic polypeptide chain

<400> SEQUENCE: 2

Asp Asp Asp Asp Asp Glu Glu Lys Glu Glu Glu Glu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: hydrophilic polypeptide chain

<400> SEQUENCE: 3

Arg Arg Arg Arg Arg Glu Asp Lys Lys Lys Lys Lys
1               5                   10